US00PP20601P2

(12) United States Plant Patent
Horner

(10) Patent No.: US PP20,601 P2
(45) Date of Patent: Dec. 22, 2009

(54) ROSE PLANT NAMED 'HORMETEORIC'

(50) Latin Name: *Rosa hybrida*
Varietal Denomination: Hormeteoric

(75) Inventor: Heather Horner, Stansted (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/228,287

(22) Filed: Aug. 11, 2008

(51) Int. Cl.
*A01H 5/00* (2006.01)

(52) U.S. Cl. ..... Plt./102
(58) Field of Classification Search ..... Plt./102, Plt./107
See application file for complete search history.

*Primary Examiner*—June Hwu
(74) *Attorney, Agent, or Firm*—C. A. Whealy

(57) ABSTRACT

A new and distinct cultivar of Rose plant named 'Hormeteoric', characterized by its upright, low spreading and mounding plant habit; dense and glossy dark green-colored foliage; freely branching growth habit; freely flowering habit; large light red, pink and yellow-colored flowers; resistance to Black Spot; and good garden performance.

1 Drawing Sheet

Figure 1:
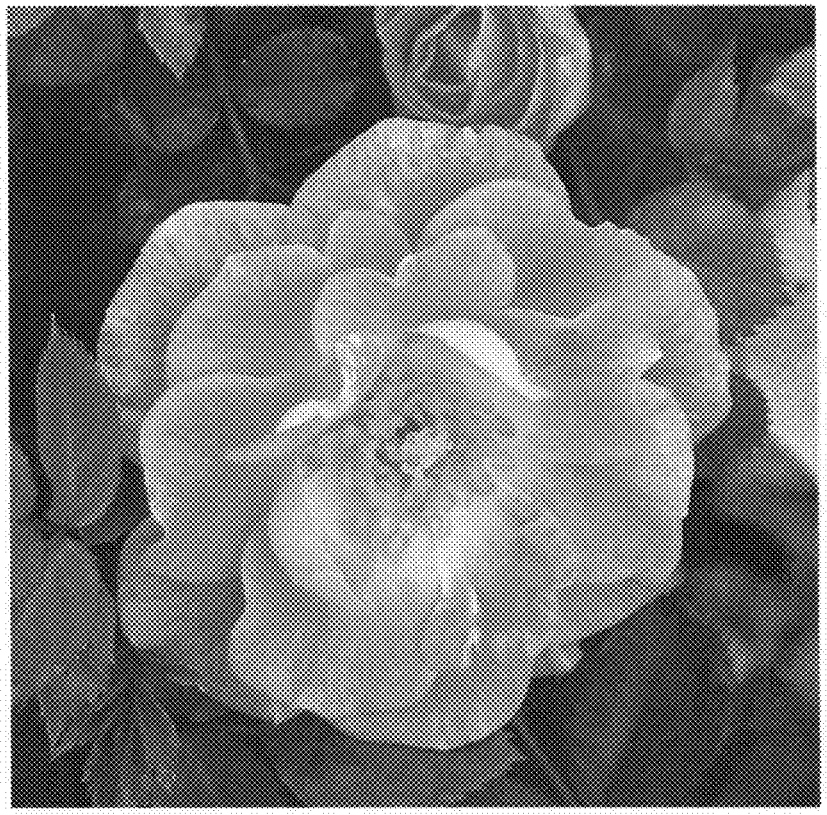

Botanical designation: *Rosa hybrida.*
Cultivar denomination: 'Hormeteoric'.

BACKGROUND OF THE INVENTION

The present Invention relates to a new and distinct cultivar of Rose plant, botanically known as *Rosa hybrida*, commercially used as an ornamental shrub, and hereinafter referred to by the name 'Hormeteoric'.

The new Rose plant is a product of a planned breeding program conducted by the Inventor in Stausted, Essex, United Kingdom. The objective of the breeding program was to develop new uniform shrub Rose varieties with attractive flower coloration.

The new Rose plant originated from a cross-pollination made by the Inventor in 1994 of *Rosa hybrida* 'Anna Ford', not patented, as the female, or seed, parent with *Rosa hybrida* 'Euphorbia', not patented, as the male, or pollen, parent. The new Rose plant was discovered and selected by the Inventor in 1995 as a single flowering plant within the progeny of the stated cross-pollination in a controlled outdoor nursery environment in Stausted, Essex, United Kingdom.

Asexual reproduction of the new Rose plant by softwood cuttings at Stausted, Essex, United Kingdom since 1995, has shown that the unique features of this new Rose plant are stable and reproduced true to type in successive generations of asexual reproduction.

SUMMARY OF THE INVENTION

The following traits have been repeatedly observed and are determined to be the unique characteristics of 'Hormeteoric'. These characteristics in combination distinguish 'Hormeteoric' as a new and distinct cultivar of Rose:

1. Upright, low spreading and mounding plant habit.
2. Dense and glossy dark green-colored foliage.
3. Freely branching growth habit.
4. Freely flowering habit.
5. Large light red, pink and yellow-colored flowers.
6. Resistant to Black Spot.
7. Good garden performance.

Plants of the new Rose differ from plants of the female parent, 'Anna Ford' in the following characteristics:

1. Plants of the new Rose are more outwardly spreading than plants of 'Anna Ford'.
2. Plants of the new Rose and 'Anna Ford' differ in flower color as plants of 'Anna Ford' have vermillion-colored flowers.

Plants of the new Rose differ from plants of the male parent, 'Euphorbia', in the following characteristics:

1. Plants of the new Rose have darker green-colored leaves than plants of 'Euphorbia'.
2. Plants of the new Rose and 'Euphorbia' differ in flower color as plants of 'Euphorbia' have orange and yellow-colored flowers.
3. Plants of the new Rose are more resistant to Black Spot than plants of 'Euphorbia'.

Plants of the new Rose can be compared to plants of the *Rosa hybrida* 'Horcoherent', disclosed in U.S. Plant Pat. No. 15,982. Plants of the new Rose differ from plants of 'Horcoherent' in the following characteristics:

1. Plants of the new Rose have darker green-colored leaves than plants of 'Horcoherent'.
2. Flowers of plants of the new Rose have more petals than flowers of plants of 'Horcoherent'.
3. Plants of the new Rose and 'Horcoherent' differ in flower color as plants of 'Horcoherent' have orange, pink and yellow-colored flowers.

BRIEF DESCRIPTION OF THE PHOTOGRAPHS

The accompanying colored photographs illustrate the overall appearance of the new Rose plant, showing the colors as true as it is reasonably possible to obtain in colored reproductions of this type. Colors in the photographs may differ slightly from the color values cited in the detailed botanical description which accurately describe the colors of the new Rose.

Figure 2:
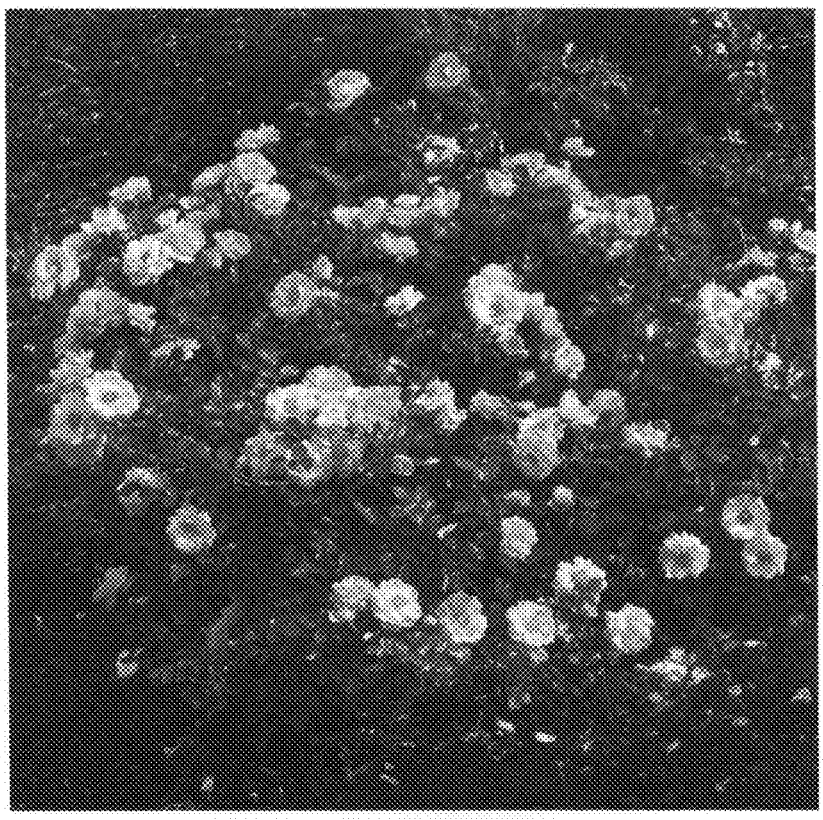

The photograph at the bottom of the sheet (FIG. 2) comprises a side perspective view of a typical plant of 'Hormeteoric' ground in an outdoor nursery.

The photograph at the top of the sheet (FIG. 1) is a close-up view of typical flowers of 'Hormeteoric'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in Grand Haven, Mich., in an outdoor nursery and under commercial production practices during the spring and summer. Plants were three years old when the photographs and description were taken. In the following description, color references are made to The Royal Horticultural Society Colour Chart, 1995 Edition, except where general terms of ordinary dictionary significance are used.

Botanical classification: *Rosa hybrida* cultivar Hormeteoric

Parentage:

*Female, or seed, parent.*—*Rosa hybrida* 'Anna Ford', not patented.

*Male, or pollen, parent.*—*Rosa hybrida* 'Euphorbia', not patented.

Propagation:

*Type.*—Softwood cuttings.

*Time to initiate roots.*—About 12 days at 25° C.

*Time to produce a rooted young plant.*—About three months at 25° C.

*Root description.*—Somewhat fibrous, medium thickness; white to brown in color.

*Rooting habit.*—Freely branching; dense.

Plant description:

*Plant form.*—Upright, low spreading and mounding perennial shrub.

*Growth habit.*—Vigorous growth habit.

*Branching habit.*—Freely basal branching habit; about 24 lateral branches per plant; dense and bushy growth habit.

*Plant height.*—About 45 cm.

*Plant width* (*spread*).—About 100 cm.

*Lateral branches.*—Length: About 45 cm. Diameter: About 5 mm. Internode length: About 2.5 cm. Strength: Strong. Texture: Smooth, glabrous. Color: Close to 143B overlain with close to 187C. Thorns: Quantity: About three per node. Shape: Triangular with sharp acuminate apices. Height: About 7 mm. Diameter, at base: About 3 mm. Color: Close to 187A.

Foliage description:

*Arrangement.*—Alternate; pinnately compound with about seven leaflets per leaf.

*Leaflet length.*—About 7.5 cm.

*Leaflet width.*—About 1.4 cm.

*Leaflet shape.*—Ovate.

*Leaflet apex.*—Acute.

*Leaflet base.*—Obtuse.

*Leaflet margin.*—Serrate.

*Leaflet texture, upper and lower surfaces.*—Smooth, glabrous.

*Leaflet luster, upper and lower surfaces.*—Glossy.

*Leaflet venation pattern.*—Pinnate.

*Leaflet color.*—Developing leaflets, upper surface: Close to 137B; margins, close to 187A. Developing leaflets, lower surface: Close to 143A; margins, close to 187A. Fully expanded leaflets, upper surface: Close to 147A; venation, close to 147A. Fully expanded leaflets, lower surface: Close to 143A; venation, close to 143A.

*Leaf petiole.*—Length: About 2.8 cm. Diameter: About 3 mm. Texture, upper and lower surfaces: Smooth, glabrous. Color, upper and lower surfaces: Close to 146C.

*Stipules.*—Length: 1.27 cm. Width: 5 mm. Color: Close to 146C.

Flower description:

*Flower type and habit.*—Rotate flowers arranged in terminal clusters with about five flowers per cluster. Flowers face mostly upright or outwardly.

*Natural flowering season.*—Plants flower in the landscape from late June until frost in Grand Haven, Mich.; during this period flowering is continuous. Flowers not persistent.

*Postproduction longevity.*—Flowers typically last about one to two weeks on the plant as well as a cut flower.

*Fragrance.*—Slightly fragrant; typical of *Rosa*; sweet, pleasant.

*Flower buds.*—Height: About 2.2 cm. Diameter: About 1 cm. Shape: Ovoid. Color: Close to 144A.

*Flowers.*—Diameter: About 5 cm. Depth: About 2.5 cm.

*Petals.*—Quantity per flower: About 21 to 24 in several whorls. Length: About 2.3 cm. Width: About 2.5 cm. Shape: Obovate. Apex: Obtuse. Base: Attenuate. Margin: Entire. Texture, upper and lower surfaces: Smooth, glabrous. Color: Developing petals, upper surface: Close to 43C; towards the base, 12A. Developing petals, lower surface: Close to 10A. Fully expanded petals, upper surface: Close to 66D, 52B and/or 55B; towards the base, close to 12A to 12B. With development, color becoming closer to 65B and towards the base, close to 13D. Fully expanded petals, lower surface: Close to 10C.

*Sepals.*—Quantity per flower: Five. Length: About 1.2 cm. Width: About 6 mm. Shape: Lanceolate. Apex: Acute. Base: Fused. Margin: Entire. Texture, upper and lower surfaces: Smooth, glabrous. Color: Developing and fully expanded sepals, upper surface: Close to 143B. Developing and fully expanded, lower surface: Close to 143C.

*Peduncles.*—Length: About 3 cm. Diameter: About 2 mm. Orientation: About 20° from vertical. Strength: Strong. Color: Close to 143A.

*Reproductive organs.*—Stamens: Quantity per flower: Numerous, about 86. Anther shape: Oblong. Anther length: Less than 1 mm. Anther color: Close to 22C. Pollen amount: Moderate. Pollen color: Close to 22C. Pistils: Quantity per flower: About 43. Pistil length: About 1.5 mm. Stigma shape: Oval. Style length: About 1.25 mm. Ovary color: Close to 143B.

*Seeds/fruits.*—Seed and fruit development has not been observed.

Pathogen/pest resistance: Plants of the new Rose have been observed to be resistant to Black Spot. Plants of the new Rose have not been observed to be resistant to pests and other pathogens common to Roses.

Garden performance: Plants of the new Rose have been observed have good garden performance and to tolerate rain, wind and temperatures ranging from about −25° C. to about 30° C.

It is claimed:

1. A new and distinct Rose plant named 'Hormeteoric,' as illustrated and described.

* * * * *